United States Patent
Hannah et al.

(10) Patent No.: US 9,322,832 B2
(45) Date of Patent: Apr. 26, 2016

(54) METHODS FOR DIAGNOSING DEGENERATIVE JOINT DISEASE

(75) Inventors: Steven Scott Hannah, Chesterfield, MO (US); Scott Sherrill, Chesterfield, MO (US); Qinghong Li, Chesterfield, MO (US); Peichuan Sun, St. Louis, MO (US)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 14/116,281

(22) PCT Filed: May 8, 2012

(86) PCT No.: PCT/US2012/036863
§ 371 (c)(1),
(2), (4) Date: Feb. 6, 2014

(87) PCT Pub. No.: WO2012/154705
PCT Pub. Date: Nov. 15, 2012

(65) Prior Publication Data
US 2014/0147865 A1 May 29, 2014

Related U.S. Application Data

(60) Provisional application No. 61/518,707, filed on May 10, 2011.

(51) Int. Cl.
| | | |
|---|---|---|
| *G01N 33/00* | (2006.01) | |
| *G01N 33/564* | (2006.01) | |
| *G01N 33/68* | (2006.01) | |
| *G01N 33/50* | (2006.01) | |

(52) U.S. Cl.
CPC .......... *G01N 33/6893* (2013.01); *G01N 33/564* (2013.01); *G01N 33/6827* (2013.01); *G01N 33/6866* (2013.01); *G01N 33/6869* (2013.01); *G01N 2333/522* (2013.01); *G01N 2333/55* (2013.01); *G01N 2333/57* (2013.01); *G01N 2800/102* (2013.01)

(58) Field of Classification Search
None
See application file for complete search history.

(56) References Cited

U.S. PATENT DOCUMENTS

| | | | |
|---|---|---|---|
| 5,756,361 A | | 5/1998 | Winterbottom et al. |
| 5,965,379 A | * | 10/1999 | Tamarkin et al. ............ 435/7.93 |
| 5,989,294 A | | 11/1999 | Marlow |
| 2007/0225206 A1 | | 9/2007 | Ling et al. |
| 2008/0199426 A1 | | 8/2008 | Sukhatme et al. |
| 2008/0227747 A1 | | 9/2008 | Tabbiner |
| 2009/0221904 A1 | | 9/2009 | Shealy et al. |
| 2010/0136001 A1 | | 6/2010 | Sukhatme et al. |
| 2010/0292154 A1 | | 11/2010 | Millett et al. |
| 2011/0065609 A1 | * | 3/2011 | Roudier et al. ................ 506/18 |

FOREIGN PATENT DOCUMENTS

| | | |
|---|---|---|
| WO | 2011109738 A1 | 9/2011 |
| WO | 2011143104 A1 | 11/2011 |

OTHER PUBLICATIONS

N. Hegemann: "Biomarkers of joint tissue metabolism in canine osteoarthritis and arthritic joint disorders", Osteoarthritis and Cartilage, vol. 10, No. 9, Sep. 1, 2002, pp. 714-721.

Zhang, Ying, e al. Serum levels of IL-1, TNF-a, IL-2, IFN-y and neopterin in patients with rheumatoid arthritis, The Department of Endocrinology, The Second Affiliated Hospital of Zhejiang University School of Medicine Hangzhou China. Dec. 25, 2003.

Written Opinion and International Search Report PCT/US2012/036863, Jul. 6, 2012.

* cited by examiner

*Primary Examiner* — Christine J Saoud
*Assistant Examiner* — Jegatheesan Seharaseyon
(74) *Attorney, Agent, or Firm* — Ronald A. Burchett; Julie M. Lappin

(57) ABSTRACT

The invention provides methods for diagnosing degenerative joint disease in an animal by collecting a saliva sample from an animal; determining the amount of at least one diagnostic agent selected from the group consisting of interferon gamma, interferoninducible protein-10, interleukin-2, and total saliva protein in the saliva sample; comparing the amount of diagnostic agent found in the saliva sample to a corresponding amount of the same diagnostic agent found in a saliva sample from one or more comparable control animals that do not suffer from degenerative joint disease; and diagnosing that the animal is susceptible to or suffering from degenerative joint disease if the amount of diagnostic agent in the saliva sample from the animal is greater than the amount of same diagnostic agent found in the saliva sample from the one or more comparable control animals.

11 Claims, No Drawings

METHODS FOR DIAGNOSING DEGENERATIVE JOINT DISEASE

CROSS REFERENCE TO RELATED APPLICATIONS

This application is a national stage application under 35 USC §371 of PCT/US2012/036863 filed on May 8, 2012 and claims priority to U.S. Provisional Application No. 61/518,707 filed May 10, 2011, the disclosures of which are incorporated herein by this reference.

BACKGROUND OF THE INVENTION

1. Field of the Invention

The invention relates generally to methods for diagnosing disease and particularly to methods for diagnosing degenerative joint disease.

2. Description of Related Art

Methods for diagnosing joint related conditions are known in the art. WO28049225A1 discloses methods for prognosing osteoarthritis by determining the cellular localization of pituitary homeobox transcription factor 1 (pitx-1) repressor protein or complex, e.g., prohibitin or prohibitone in a sample, e.g., articular chondrocytes sample. US20070248986A1 discloses methods for predicting the likelihood of developing rheumatoid arthritis for individuals with recent-onset undifferentiated arthritis by determining a set of clinical parameter values and a predicted risk for developing rheumatoid arthritis by correlating the parameter values with predefined risk values associated with ranges of parameter values, e.g., serum levels of C-reactive protein, Rheumatoid factors, anti-CCP antibodies, age, gender, localization of the joint complaints, length of morning stiffness, and number of tender and/or swollen joints. U.S. Pat. No. 7,005,274 discloses diagnostic methods for early detection of a risk for developing an arthritic disorder in humans and screening assays for therapeutic agents useful in the treatment of arthritic disorders by comparing the levels of one or more indicators of altered mitochondrial function, e.g., enzymes such as mitochondrial enzymes, ATP biosynthesis factors, mitochondrial mass, mitochondrial number, mitochondrial DNA content, cellular responses to elevated intracellular calcium and to apoptogens, and free radical production. US20040242987A1 discloses methods for predicting bone or articular disease affecting musculoskeletal system (e.g., osteoporosis) by obtaining micro and macro-structural or biomechanical parameters obtained from images of a joint and analyzing at least two of the parameters, e.g., macro anatomical parameters and biomechanical parameters. Other known methods include physical examination, plain film radiography, computed axial tomography (CAT) scans, magnetic resonance imaging (MRI) scans, contrast radiography, and arthroscopy.

Diagnosing joint related conditions such as degenerative joint disease in animals using physical examination and plain film radiography is common. In particular, these methods are the primary tools for diagnosing osteoarthritis in various animals such as dogs. However, affected animals often do not exhibit overt lameness or other symptoms indicating degenerative joint disease. Unfortunately, this means that observable clinical signs are insufficient to support a presumptive diagnosis of degenerative joint disease, e.g., osteoarthritis. Further, plain film radiography, while it is the most frequently used screening technology, reveals bony changes but often does not demonstrate changes in soft tissues such as the joint capsule, thus complicating routine diagnosis. Similarly, CAT and MRI scans are expensive and often not widely available. Contrast radiography and arthroscopy add a degree of invasiveness. In some animals such as dogs, these additional modalities always require some form of restraint such as anesthesia, thus adding cost, complexity, and risk. Given these limitations to known methods, degenerative joint disease often goes undiagnosed. There is, therefore, a need for new methods for diagnosing degenerative joint disease in animals.

SUMMARY OF THE INVENTION

It is, therefore, an object of the present invention to provide methods for diagnosing degenerative joint disease in animals.

This and other objects are achieved using methods for diagnosing degenerative joint disease in an animal that involve collecting a saliva sample from an animal; determining the amount of at least one diagnostic agent selected from the group consisting of interferon IFNγ, IP-10, IL-2, and TSP in the saliva sample; comparing the amount of diagnostic agent found in the saliva sample to a corresponding amount of the same diagnostic agent found in a saliva sample from one or more comparable control animals that do not suffer from degenerative joint disease; and diagnosing that the animal is susceptible to or suffering from degenerative joint disease if the amount of diagnostic agent in the saliva sample from the animal is greater than the amount of same diagnostic agent found in the saliva sample from the one or more comparable control animals.

Other and further objects, features, and advantages of the present invention will be readily apparent to those skilled in the art.

DETAILED DESCRIPTION OF THE INVENTION

Definitions

The term "animal" means any animal susceptible to or suffering from degenerative joint disease, including human, avian, bovine, canine, equine, feline, hicrine, lupine, murine, ovine, or porcine animals.

The term "comparable control animal" means an animal of the same species and type or an individual animal evaluated at two different times.

The term "joint" means a connection between two or more adjacent parts of an animal skeleton, whether bone or cartilage.

The term "degenerative joint disease" means a disease or other condition caused by inflammation, breakdown, and eventual loss of the cartilage of the joints. Degenerative joint disease is also known as osteoarthritis or degenerative arthritis The term "companion animals" means domesticated animals such as dogs, cats, birds, rabbits, guinea pigs, ferrets, hamsters, mice, gerbils, pleasure horses, cows, goats, sheep, donkeys, pigs, and more exotic species kept by humans for company, amusement, psychological support, extrovert display, and all of the other functions that humans need to share with animals of other species.

As used herein, ranges are used herein in shorthand, so as to avoid having to list and describe each and every value within the range. Any appropriate value within the range can be selected, where appropriate, as the upper value, lower value, or the terminus of the range.

As used herein, the singular form of a word includes the plural, and vice versa, unless the context clearly dictates otherwise. Thus, the references "a", "an", and "the" are generally inclusive of the plurals of the respective terms. For example, reference to "a joint" or "a method" includes a plurality of such "joints" or "methods." Similarly, the words "comprise", "comprises", and "comprising" are to be interpreted inclusively rather than exclusively. Likewise the terms "include", "including" and "or" should all be construed to be inclusive, unless such a construction is clearly prohibited from the context.

The methods and compositions and other advances disclosed here are not limited to particular methodology, protocols, and reagents described herein because, as the skilled artisan will appreciate, they may vary. Further, the terminology used herein is for the purpose of describing particular embodiments only, and is not intended to, and does not, limit the scope of that which is disclosed or claimed.

Unless defined otherwise, all technical and scientific terms, terms of art, and acronyms used herein have the meanings commonly understood by one of ordinary skill in the art in the field(s) of the invention, or in the field(s) where the term is used. Although any compositions, methods, articles of manufacture, or other means or materials similar or equivalent to those described herein can be used in the practice of the present invention, the preferred compositions, methods, articles of manufacture, or other means or materials are described herein.

All patents, patent applications, publications, technical and/or scholarly articles, and other references cited or referred to herein are in their entirety incorporated herein by reference to the extent allowed by law. The discussion of those references is intended merely to summarize the assertions made therein. No admission is made that any such patents, patent applications, publications or references, or any portion thereof, are relevant, material, or prior art. The right to challenge the accuracy and pertinence of any assertion of such patents, patent applications, publications, and other references as relevant, material, or prior art is specifically reserved.

The Invention

In one aspect, the invention provides methods for diagnosing degenerative joint disease in animals. The methods comprise collecting a saliva sample from an animal; determining the amount of at least one diagnostic agent selected from the group consisting of interferon gamma (IFNγ), interferon-inducible protein-10 (IP-10), interleukin-2 (IL-2), and total saliva protein (TSP) in the saliva sample; comparing the amount of diagnostic agent found in the saliva sample to a corresponding amount of the same diagnostic agent found in a saliva sample from one or more comparable control animals that do not suffer from degenerative joint disease; and diagnosing that the animal is susceptible to or suffering from degenerative joint disease if the amount of diagnostic agent in the saliva sample from the animal is greater than the amount of same diagnostic agent found in the saliva sample from the one or more comparable control animals.

The invention is based upon the discovery that the diagnostic agents of the invention are present in the saliva of an animal and that the amount of the diagnostic agents in saliva serves as a biochemical indicator for diagnosing degenerative joint disease by indicating or predicting the threshold for degenerative joint disease. The invention allows veterinary and other clinicians to perform tests for these "biomarkers" in saliva and determine whether the animal is susceptible to or suffering from degenerative joint disease and whether there is a need for further diagnostics or treatment. Having established the need for further diagnostics or treatments, the cost and risk of such further diagnostics or treatments are justified.

In various embodiments, one or more comparable control animals that are not the animal being evaluated for degenerative joint disease and that have been determined not to suffer from degenerative joint disease are evaluated for at least one or the diagnostic agents and the results of such evaluations are used as a baseline value for comparison with the results from an animal being evaluated for one or more of the diagnostic agents. In preferred embodiments, the baseline value for the diagnostic agents is determined by evaluating numerous comparable control animals.

In another, the amount of at least one of the diagnostic agents are determined for an animal at various times throughout the animal's life and the results used to determine if the animal is susceptible to or suffering from degenerative joint disease, e.g., if the amount of at least one diagnostic agent increases as the animal ages, the animal can be diagnosed as susceptible to or suffering from degenerative joint disease. In preferred embodiments, the animal is evaluated periodically and the results for the diagnostic agents are recorded. Then, if a subsequent evaluation shows that the amount of one or more diagnostic agents has increased since the last evaluation(s), the animal is diagnosed as susceptible to or suffering from degenerative joint disease.

In one embodiment, the animal is determined to be susceptible to or suffering from degenerative joint disease if the amount of IFNγ in the saliva of the animal being evaluated is at least 1.2 times the amount of IFNγ found in the saliva of one or more comparable control animals. In various embodiments, the amount of IFNγ in the animal being evaluated is from about 1.2 to about 20 times the amount of IFNγ found in the saliva of one or more comparable control animals.

In another embodiment, the animal is determined to be susceptible to or suffering from degenerative joint disease if the amount of IP-10 in the saliva of the animal being evaluated is at least 1.4 times the amount of IP-10 found in the saliva of one or more comparable control animals. In various embodiments, the amount of IP-10 in the animal being evaluated is from about 1.4 to about 20 times the amount of IP-10 found in the saliva of one or more comparable control animals.

In a further embodiment, the animal is determined to be susceptible to or suffering from degenerative joint disease if the amount of IL-2 in the saliva of the animal being evaluated is at least 1.6 times the amount of IL-2 found in the saliva of one or more comparable control animals. In various embodiments, the amount of IL-2 in the animal being evaluated is from about 1.6 to about 20 times the amount of IL-2 found in the saliva, of one or more comparable control animals.

In another embodiment, the animal is determined to be susceptible to or suffering from degenerative joint disease if the amount of TSP in the saliva of the animal being evaluated is at least 1.8 times the amount of TSP found in the saliva of one or more comparable control animals. In various embodiments, the amount of TSP in the animal being evaluated is from about 1.8 to about 20 times the amount of TSP found in the saliva of one or more comparable control animals.

While the use of one of the diagnostic agents is sufficient for diagnosing degenerative joint disease, the use of two or more of such diagnostic agents is encompassed within the invention and may be preferred in many circumstances. In one embodiment, the diagnosis is based upon two diagnostic agents, in another three diagnostic agents, in another all four diagnostic agents. The diagnostic agents can be evaluated and used for a diagnosis in any combination. In one preferred embodiment, the diagnosis is based upon two diagnostic agents, i.e., IFNγ and IP-10. In another preferred embodiment, the diagnosis is based upon all four diagnostic agents.

Any joint subject to failure can be diagnosed using the methods of the present invention. Typical joints include, but are not limited to, gliding joints (Arthrodia), hinge joints (Ginglymus), condyloid joints (Condylarthrosis), saddle-shaped joints (Articulus sellaris), ball and socket joints (Enarthrosis), and pivot joints (Trochoides). Specific joints include, but are not limited to, knee, elbow, interphalangeal, metacarpophalangeal, wrist, carpo-metacarpal, thumb, shoulder, hip, temporo-mandibular, and radio-ulnar joints. Shoulder and hip joints are particularly susceptible to degenerative joint disease.

In various embodiments, the animal is a human or companion animal. Preferably, the companion animal is a canine such as a dog or a feline such as a cat.

Methods for collecting saliva from an animal are known to skilled artisans, e.g., using a toy or similar device that interacts orally with an animal as a playful activity or simply using a swab or similar device to collect a saliva sample. One such device is disclosed in U.S. Provisional Patent Application Ser. No. 61/455,152 entitled Oral Engagement Assembly.

Methods for determining amount of the diagnostic agents in saliva are well known in the art. Various chemical analyzers, manual or automated, are available commercially to skilled artisans for measuring concentrations of the diagnostic agents of the invention in saliva, e.g., ELISA tests. Examples of such methods are given in the EXAMPLES herein.

EXAMPLES

The invention can be further illustrated by the following examples, although it will be understood that these examples are included merely for purposes of illustration and are not intended to limit the scope of the invention unless otherwise specifically indicated.

Example 1

Saliva Collection: A commercial saliva collection device called SALIVETTE® (SARSTEDT, Germany) was employed to collect saliva from dogs. The dog's mouth was opened and the SALIVETTE® cotton swab was inserted into the mouth such that the animal chewed it for about 30 to 45 seconds. Then, the SALIVETTE® was removed and transferred to the SALIVETTE® collection tube. Saliva was isolated immediately by spinning the collection tube at 1,000 g for 2 minutes. Finally, the saliva sample collected in the bottom tip of the collection tube was transferred to a fresh micro tube and the micro tube was immediately frozen at −80° C. degree for further analysis.

Canine Cytokine Analysis: 14 cytokines were measured with the LUMINEX multiplex canine cytokine panel manufactured by Millipore, Catalog No. CCYTO-90K. The standard procedure from the manufacturer was followed. All saliva samples were spun in a microcentrifuge at 14,000 g for 2 minutes right before use. Then, supernatants were carefully transferred to a fresh microtube, diluted with LUMINEX Assay Buffer (Millipore Catalog No. L-AB) at 1 to 3 dilutions. Individual samples were loaded on a pre-wet 96 well filter plate (provided by manufacturer) with Canine Cytokine Quality Controls 1 & 2 (Millipore Catalog No. LCC-6090) and standards (Millipore Catalog No. LCC-8090). The plates were processed as directed by the manufacturer's manual. Saliva samples were mixed with beads immobilized with antibodies against 14 cytokine/chemokines (GM-CSF, IFNγ, KC, IP-10, IL-2, IL-4, IL-6, IL-7, IL-8, IL-10, IL-15, IL-18, MCP-1 and TNFα) and incubated overnight with robust shaking on a lab titer plate shaker (Lab-Line Instruments Model No. 4625) at 4° C. The next day, Canine Cytokine Detection Antibodies (Catalog No. LCC-1090) were added to the plate after the plate was washed with LUMINEX Wash Buffer (Catalog No. L-WB). Then, the plate was sealed and incubated for 1 hour at room temperature with robust shaking on the titer plate shaker. Afterward, Streptavidin-Phycoerythrin (Catalog No. L-SAPE3) was added to the plate and the plate was covered with a lid (provided by manufacturer) to prevent exposure to light. The covered plate was then incubated for another 30 minutes with robust agitation. After that incubation, the plate was washed with LUMINEX Wash Buffer and the beads in the wells were resuspended in LUMINEX sheath fluid and read on a LUMINEX 100 IS reader. The cytokine concentrations of saliva samples were calculated by software named LUMINEX xPONENT (version 3.1.871.0).

Substance P ELISA: Canine saliva was analyzed with a commercial ELISA kit-Parameter Substance P Assay (R&D Systems, Catalog No. KGE 007). For this assay, all canine saliva samples were diluted at 20 folds in the Calibrator Diluent RD5-45 (included in the kit). Standards and detection antibodies (included in the kit) are prepared in the same diluents as directed in the kit. That is a competitive ELISA. During a 3 hour incubation, the substance P (SP) in the samples or standards will compete with a fixed amount of horseradish peroxisase—labeled Substance P (HRP-SP) for binding sites on a mouse anti-Substance P (SP) antibody. After the 3 hour incubation, unbound/excess SP-HRP was washed away, only the bound SP and SP-HRP could link to the antibody pre-coated 96 well plate (included in the kit) by the interaction between the plate coating antibody and the mouse anti-SP antibody. Finally, a chromogen (tetramethylbenzidine) solution was added to the 96 well plate. Only the bound SP-HRP, but not bound SP, would react with this chromogen substrate to develop a blue color. After stopping the reaction with 2N sulfuric acid, optical density (OD) was measured at a wavelength of 450 nm by a plate reader (BIO-TEK POWER WAVE X). The concentration of SP in a sample is inversely proportional to the OD and was calculated from the standard curve generated by a serially diluted SP standard solution using a software named KC Junior (version 1.41).

IgA ELISA: Saliva IgA was analyzed using a commercial canine ELISA kit (Bethyl Laboratories, Inc., Catalog No. E40-104), all antibodies and standards were included in the kit. Common ELISA buffers were prepared internally with chemical purchased from Sigma-Aldrich (Saint Louis, Mo.) or purchased directly from other vendors as stated:

(1) Coating Buffer, 0.05 M Carbonate-Bicarbonate, pH 9.6;
(2) Wash Solution, 50 mM Tris, 0.14 M NaCl, 0.05% Tween 20, pH 8.0;
(3) Blocking Solution, 50 mM Tris, 0.14 M NaCl, 1% Bovine Serum Albumin (BSA), pH 8.0; 4) Sample/Conjugate Diluent, 50 mM Tris, 0.14 M NaCl, 1% BSA, 0.05% Tween 20;
(4) Enzyme SubstrateTMB, pre-made solution SUREBLUE (peroxidase substrate) (KPL, Catalog No. 52-00-03); and
(5) Stop Solution, 4N sulfuric acid solution.

Standard sandwich ELISA procedure was followed. Coated a 96 well ELISA plate with freshly made anti-canine IgA antibody solution in Coating Buffer for an hour, then washed the plate with Wash Solution, added Blocking Solution and incubated for 30 minutes. After washes, added pre-diluted samples or standard solutions to wells of the plate. Most saliva samples were diluted in Sample/Conjugate Diluents at 1 to 5000, adjustments were made when measured IgA concentrations were out of the dynamic range of standard curve. After 1 hour incubation and another wash step, HRP conjugated detection antibody solution (diluted in Sample/Conjugate Diluent) was added to that plate and incubated for an hour. After washes, the colorimetric development of this plate was initiated by adding Enzyme SubstrateTMB. After 10 to 15 minutes development (till a proper dark blue colors appeared), the color reaction was stopped by adding Stop Solution. By the end, OD of this plate was measured by a plate reader (BIO-TEK POWER WAVE) at 450 nm. Concentrations of IgA in the samples were calculated using a KC Junior software (version 1.41).

Total Saliva Protein measurements were determined using a commercial BCA protein assay kit (Thermo Scientific, Catalog No. 23225) as directed in the manual. Prepared a serial dilution of Bovine Serum Albumin (BSA) standards (at a range of 0 to 2 mg/ml) in distilled and deionized water from the BSA standard stock provided in the kit. Then, diluted the saliva samples to a proper fold to fit detected protein concentrations into the BSA standard curve. It may take several times to find the right dilution for individual samples. After that, mixed BCA Protein Assay Reagent A (Thermo Scientific, Catalog No. 23221) and reagent B (Thermo Scientific, Catalog No. 23224) at 50 to 1 (v/v) well in a fresh plastics test tube by vortex. After that, diluted samples or BSA standards were added to the wells of a clear bottom plastic 96 well plate, then the mixture of reagent A and B was added to these wells, incubated the plate at room temperature for 30 minutes. During the incubation, the copper sulfate pentahydrate in the reagent B reacted with protein in the samples, $Cu^{2+}$ was reduced to $Cu^{1+}$ and then Bicinchonic acid (BCA) in reagent A reacts with the reduced (cuprous) cation to form purple-color solution, which exhibits a strong linear absorbance at 562 nm with increasing protein concentrations. The plate with samples and standards can be read on a plate reader (BIO-TEK POWER WAVE X) at a wavelength of 562 nm. Concentrations of total saliva protein in the samples were calculated using a KCJunior software (version 1.41).

Statistical Analysis: Student T tests was performed with an analysis software package "R" (www.r-project.org) on all data generated in this study. Statistically significant differences between two groups were investigated for individual saliva biomarkers. The results are shown in Table 1 and Table 2. Referring to Table 1 and Table 2, the data show that IFNγ, IP-10, IL-2, and total saliva protein are significantly different between animals with and animals without degenerative joint disease. The substances, therefore, serve as biomarkers for degenerative joint disease in animals.

TABLE 1

| Animal ID | Sex | Breed | Age | Health Status | BCS Score | Total Saliva Protein (mg/ml) | Saliva IgA (µg/ml)* |
|---|---|---|---|---|---|---|---|
| 28 | F/s | Bor Ter | 14 | DJD | | 15.63 | 5650.03 |
| 48 | M/n | GRSHPD | 10 | DJD | BCS 4 | 1.29 | 2003.24 |
| 30 | M/n | LAB | 14 | DJD, Dementia | BCS 6 | 0.87 | 372.41 |
| 31 | M/n | LAB | 10 | DJD | BCS 7 | 0.57 | 493.85 |
| 32 | F/s | LAB | 10 | DJD | BCS 5 | 1.07 | 1562.29 |
| 35 | F/s | LAB | 14 | DJD | BCS 5 | 2.88 | 429.12 |
| 36 | F/s | LAB | 14 | DJD | BCS 5 | 2.62 | 2774.87 |
| 37 | F/s | LAB | 13 | DJD | BCS 5 | 1.49 | 2823.45 |
| 38 | F/s | LAB | 12 | DJD | BCS 5 | 0.73 | 1642.76 |
| 46 | F/s | LAB | 14 | DJD | BCS 6 | 1.79 | 2317.79 |
| 47 | M/n | LAB | 14 | DJD | BCS 4 | 1.40 | 1694.37 |
| 29 | F/s | SET | 14 | DJD, mammary tumors | BCS 4 | 0.56 | 283.66 |
| 34 | M/n | SET | 14 | DJD | BCS 5 | 0.89 | 541.31 |
| 39 | F/s | SET | 14 | DJD | BCS 4 | 1.09 | 828.66 |
| 44 | F/s | SET | 8 | Arthritis | BCS 6 | 13.5 | 3297.19 |
| 33 | F/s | SIB | 6 | DJD | BCS 5 | 2.78 | 2048.21 |
| 2B | F/s | SET | 14 | Control | BCS 5 | 1.78 | 533.45 |
| 3B | F/s | LAB | 12 | Control | BCS 5 | 1.56 | 336.50 |
| 4B | F/s | LAB | 10 | Control | BCS 5 | 1.42 | 1235.88 |
| 11B | F/s | LAB | 2 | Control | BCS 5 | 0.44 | 362.20 |
| 12B | F/s | LAB | 2 | Control | BCS 5 | 0.37 | 361.27 |
| 72 | M/n | LAB | 6 | Control | BCS 5 | 0.74 | 724.12 |
| 81 | M | LAB | 7 | Control | BCS 5 | 1.60 | 3839.68 |
| 53 | M/n | LAB | 9 | Control | BCS 6 | 1.79 | 1183 |
| 57 | F/s | LAB | 10 | Control | BCS 6 | 0.82 | 1652 |
| 64 | F | LAB | 6 | Control | BCS 6 | 0.59 | 418 |
| 65 | F | LAB | 4 | Control | BCS 6 | 0.58 | 474 |
| 72 | M/n | LAB | 6 | Control | BCS 5 | 0.74 | 724 |
| 81 | M | LAB | 7 | Control | BCS 5 | 1.60 | 3840 |
| 1B | F/s | LAB | 14 | Control | BCS 5 | 3.12 | 5844 |
| 15B | F/s | LAB | 1 | Control | BCS 5 | 2.89 | 895 |
| 8B | F/s | SET | 4 | Control | BCS 5 | 1.43 | 5295.47 |
| 17B | M/n | SET | 14 | Control | BCS 4 | 2.20 | 4815.07 |
| 19B | F/s | SET | 13 | Control | BCS 3 | 2.27 | 3005.73 |
| 68 | M/n | SET | 10 | Control | BCS 5 | 0.74 | 284.30 |
| 73 | M/n | SET | 5 | Control | BCS 5 | 3.12 | 10294.31 |
| 74 | M/n | SET | 4 | Control | BCS 5 | 1.43 | 3575.66 |
| 78 | M/n | SET | 2 | Control | BCS 5 | 1.14 | 2162.50 |

| GM-CSF (pg/ml) | IFNγ (pg/ml) | IL-10 (pg/ml) | IL-15 (pg/ml) | IL-18 (pg/ml) | IL-2 (pg/ml) | IL-4 (pg/ml) |
|---|---|---|---|---|---|---|
| 39.02 | 4.4 | 1.6 | 106.65 | 16.47 | 38.33 | 28.8 |
| 199.84 | 4.4 | 39.41 | 25.95 | 42.12 | 6.4 | 28.8 |

TABLE 1-continued

| | | | | | | |
|---|---|---|---|---|---|---|
| 49.95 | 26.24 | 1.6 | 31.11 | 7.15 | 36.58 | 28.8 |
| 25.34 | 98.48 | 1.6 | 36.46 | 14.38 | 27.61 | 28.8 |
| 29.91 | 3.55 | 1.6 | 19.04 | 2.28 | 12.81 | 28.8 |
| 48.13 | 42.18 | 16.22 | 53.42 | 14.36 | 53.59 | 28.8 |
| 41.76 | 4.4 | 1.6 | 32.31 | 21.03 | 15.68 | 28.8 |
| 22.16 | 4.4 | 1.6 | 24.56 | 8.44 | 14.09 | 28.8 |
| 85.11 | 147.40 | 3.92 | 72.94 | 99.14 | 162.01 | 86.88 |
| 14.4 | 4.4 | 31.11 | 14.8 | 38.75 | 6.4 | 28.8 |
| 14.4 | 4.4 | 22.70 | 14.8 | 16.33 | 6.4 | 28.8 |
| 36.27 | 23.27 | 1.6 | 50.51 | 11.00 | 28.73 | 28.8 |
| 39.08 | 4.4 | 1.6 | 14.8 | 7.13 | 15.91 | 28.8 |
| 41.05 | 10.16 | 0.19 | 38.53 | 27.98 | 50.80 | 28.8 |
| 14.4 | 4.4 | 4.84 | 27.58 | 12.45 | 6.4 | 28.8 |
| 60.41 | 8.88 | 1.6 | TOO high | 24.31 | 39.67 | 28.8 |
| 18.775 | 60.395 | 1.6 | 14.8 | 5.805 | 37.98 | 28.8 |
| 56.855 | 103.23 | 2.03 | 77.77 | 14.575 | 48.575 | 28.8 |
| 51.75 | 100.045 | 1.31 | 47.59 | 9.97 | 47.735 | 28.8 |
| 93.365 | 89.745 | 19.855 | 52.815 | 49.675 | 68.045 | 138.93 |
| 54.49 | 66.52 | 19.5 | 20.18 | 29.39 | 76.17 | 138.93 |
| DUA | DUA | DUA | DUA | DUA | DUA | DUA |
| DUA | DUA | DUA | DUA | DUA | DUA | DUA |
| 29.84 | 14.40 | 1.55 | 46.18 | 17.72 | 69.72 | 106.09 |
| 29.45 | 47.23 | 1.60 | 11.56 | 10.58 | 22.43 | 28.80 |
| DUA | DUA | DUA | DUA | DUA | DUA | DUA |
| DUA | DUA | DUA | DUA | DUA | DUA | DUA |
| DUA | DUA | DUA | DUA | DUA | DUA | DUA |
| DUA | DUA | DUA | DUA | DUA | DUA | DUA |
| 52.00 | 56.50 | 1.60 | 14.80 | 14.20 | 76.18 | 28.80 |
| 19.71 | 25.74 | 4.55 | 30.19 | 4.60 | 25.96 | 12.37 |
| 22.955 | 37.665 | 1.6 | 14.8 | 4.69 | 19.335 | 28.8 |
| 97.14 | 125.91 | 10.34 | 113.41 | 21.84 | 157.59 | 28.8 |
| 54.43 | 4.4 | 1.6 | 52.26 | 9.30 | 72.57 | 28.8 |
| DUA | DUA | DUA | DUA | DUA | DUA | DUA |
| DUA | DUA | DUA | DUA | DUA | DUA | DUA |
| DUA | DUA | DUA | DUA | DUA | DUA | DUA |
| DUA | DUA | DUA | cDUA | DUA | DUA | DUA |

| IL-4 (pg/ml) | IL-6 (pg/ml) | IL-7 (pg/ml) | IL-8 (pg/ml) | IP-10 (pg/ml) | KC (pg/ml) | MCP-1 (pg/ml) | TNF-a (pg/ml) |
|---|---|---|---|---|---|---|---|
| 28.8 | 12.1 | 9.43 | 20526.36 | 75.56 | 2906.47 | 185.41 | 53.05 |
| 28.8 | 67.93 | 25.88 | 5347.21 | 44.68 | 1516.46 | 86.42 | 49.60 |
| 28.8 | 12.1 | 11.73 | 3854.66 | 2.4 | 1054.65 | 82.13 | 21.93 |
| 28.8 | 12.1 | 25.26 | 4092.34 | 60.33 | 539.35 | 65.91 | 18.01 |
| 28.8 | 12.1 | 6.00 | 2408.24 | 2.4 | 1281.21 | 63.40 | 6.91 |
| 28.8 | 61.36 | 14.41 | 1578.69 | 120.57 | 1249.71 | 68.87 | 4.59 |
| 28.8 | 12.1 | 30.47 | 4251.10 | 95.79 | 620.63 | 56.54 | 13.29 |
| 28.8 | 12.1 | 12.30 | 6265.12 | 41.85 | 3034.49 | 71.32 | 39.44 |
| 86.88 | 12.1 | 37.00 | 3294.73 | 80.66 | 1833.44 | 124.43 | 8.28 |
| 28.8 | 49.12 | 34.76 | 4824.00 | 2.4 | 1654.22 | 69.52 | 25.10 |
| 28.8 | 26.13 | 14.21 | 5785.39 | 27.14 | 1277.45 | 47.76 | 10.18 |
| 28.8 | 12.1 | 8.17 | 4106.65 | 2.4 | 2184.59 | 69.21 | 4.13 |
| 28.8 | 12.1 | 13.66 | 2663.76 | 2.4 | 926.64 | 44.35 | 8.23 |
| 28.8 | 12.1 | 10.32 | 1573.32 | 129.12 | 551.25 | 68.35 | 12.96 |
| 28.8 | 18.80 | 9.05 | 13365.17 | 2.4 | 1755.42 | 299.53 | 346.56 |
| 28.8 | 12.1 | 17.38 | 3941.90 | 161.22 | 836.66 | 62.60 | 39.38 |
| 28.8 | 12.1 | 5.705 | 2008.645 | 2.4 | 1912.415 | 51.04 | 34.35 |
| 28.8 | 12.1 | 11.625 | 2369.905 | 2.4 | 1179.165 | 77.575 | 173.705 |
| 28.8 | 12.1 | 4.17 | 1639.415 | 2.4 | 2573.56 | 73.18 | 34.995 |
| 138.93 | 12.1 | 22.43 | 3994.99 | 2.4 | 1058.355 | 100.17 | 8.44 |
| 138.93 | 12.1 | 7.26 | 1211.25 | 2.4 | 322.87 | 60.69 | 4.97 |
| DUA | DUA | DUA | DUA | DUA | DUA | DUA | DUA |
| DUA | DUA | DUA | DUA | DUA | DUA | DUA | DUA |
| 106.09 | 12.10 | 22.45 | 3550.94 | 92.07 | 644.57 | 124.32 | 21.45 |
| 28.80 | 12.10 | 17.21 | 3475.75 | 2.40 | 870.09 | 76.38 | 0.40 |
| DUA | DUA | DUA | DUA | DUA | DUA | DUA | DUA |
| DUA | DUA | DUA | DUA | DUA | DUA | DUA | DUA |
| DUA | DUA | DUA | DUA | DUA | DUA | DUA | DUA |
| DUA | DUA | DUA | DUA | DUA | DUA | DUA | DUA |
| 28.80 | 12.10 | 26.21 | 3732.87 | 2.40 | 1155.56 | 100.86 | 294.79 |
| 12.37 | 33.00 | 4.60 | 469.39 | 80.25 | 292.56 | 31.76 | 0.40 |
| 28.8 | 12.1 | 4.6 | 2469.515 | 2.4 | 3129.81 | 58.605 | 13.845 |
| 28.8 | 12.1 | 63.79 | 21111.16 | 13.53 | 2679.59 | 101.79 | 96.33 |
| 28.8 | 12.1 | 12.72 | 2778.60 | 43.89 | 1015.67 | 96.20 | 9.80 |
| DUA | DUA | DUA | DUA | DUA | DUA | DUA | DUA |
| DUA | DUA | DUA | DUA | DUA | DUA | DUA | DUA |
| DUA | DUA | DUA | DUA | DUA | DUA | DUA | DUA |
| DUA | DUA | DUA | DUA | DUA | DUA | DUA | DUA |

DUA = Data Unavailable

TABLE 2

| Saliva Biomarkers | DJD Group | | Control Group | | p value | Standard Errors |
|---|---|---|---|---|---|---|
| | Mean | Number of Animals Tested | Mean | Number of Animals Tested | | |
| Total Saliva Protein | 3.409 | 16 | 1.471 | 22 | 0.071* | 0.525 |
| Substance P | 1307.357 | 16 | 728.5 | 14 | 0.571 | 498.575 |
| Saliva IgA | 2007.653 | 16 | 2357.097 | 22 | 0.639 | 356.161 |
| GM-CSF | 48.215 | 16 | 48.397 | 12 | 0.991 | 7.58 |
| IFNγ | 24.704 | 16 | 60.982 | 12 | 0.035** | 8.706 |
| IL-10 | 9.256 | 16 | 5.595 | 12 | 0.389 | 2.072 |
| IL-15 | 37.065 | 16 | 41.363 | 12 | 0.712 | 5.646 |
| IL-18 | 24.655 | 16 | 16.029 | 12 | 0.281 | 3.913 |
| IL-2 | 32.579 | 16 | 60.191 | 12 | 0.087* | 8.034 |
| IL-4 | 32.949 | 16 | 52.227 | 12 | 0.157 | 6.731 |
| IL-6 | 23.731 | 16 | 13.842 | 12 | 0.115 | 3.112 |
| IL-7 | 18.581 | 16 | 16.898 | 12 | 0.755 | 2.612 |
| I-.8 | 5708.381 | 16 | 4067.702 | 12 | 0.44 | 1033.569 |
| IP-10 | 60.466 | 16 | 20.745 | 12 | 0.032** | 9.418 |
| KC | 1427.386 | 16 | 1402.851 | 12 | 0.943 | 165.802 |
| MCP-1 | 93.886 | 16 | 79.381 | 12 | 0.502 | 10.5 |
| TNF-a | 45.399 | 16 | 57.79 | 12 | 0.727 | 17.176 |

DJD = Degenerative Joint Disease
**significant;
*marginally significant

In the specification, there have been disclosed typical preferred embodiments of the invention. Although specific terms are employed, they are used in a generic and descriptive sense only and not for purposes of limitation. The scope of the invention is set forth in the claims. Obviously many modifications and variations of the invention are possible in light of the above teachings. It is therefore to be understood that within the scope of the appended claims, the invention may be practiced otherwise than as specifically described.

What is claimed is:

1. A method for diagnosing degenerative joint disease in an animal comprising: collecting a saliva sample from the animal; determining the amount of interferon gamma (IFNγ), interferon-inducible protein-10 (IP-10), interleukin-2 (IL-2), and total saliva protein (TSP) in the saliva sample; comparing the amount of diagnostic agent found in the saliva sample to a corresponding amount of the same diagnostic agent found in a saliva sample from one or more comparable control animals that do not suffer from degenerative joint disease; and diagnosing that the animal is susceptible to or suffering from degenerative joint disease if the amount of IFNy in the saliva is about 1.2 times to about 20 times the amount found in the saliva of the one or more comparable control animals, the amount of IP-10 in the saliva is about 1.4 times to about 20 times the amount found in the saliva of the one or more comparable control animals, the amount of IL-2 in the saliva is about 1.6 times to about 20 times the amount found in the saliva of the one or more comparable control animals, or the amount of TSP in the saliva is at about 1.8 times to about 20 times the amount found in the saliva of the one or more comparable control animals, wherein the diagnosis is based upon determining the amount of all four diagnostic agents.

2. The method of claim 1 wherein the joint is a gliding joint, hinge joint, condyloid joint, saddle-shaped joint, ball and socket joint, or pivot joint.

3. The method of claim 1 wherein the joint is a knee, elbow, interphalangeal, metacarpophalangeal, wrist, carpo-metacarpal, thumb, shoulder, hip, temporo-mandibular, or radio-ulnar joint.

4. The method of claim 1 wherein the joint is a shoulder joint.

5. The method of claim 1 wherein the joint is a hip joint.

6. The method of claim 1 wherein the animal is a human.

7. The method of claim 1 wherein the animal is a companion animal.

8. The method of claim 7 wherein the animal is a canine.

9. The method of claim 8 wherein the animal is a dog.

10. The method of claim 7 wherein the animal is a feline.

11. The method of claim 10 wherein the animal is a cat.

* * * * *